United States Patent [19]

Naarmann et al.

[11] Patent Number: 4,488,986

[45] Date of Patent: Dec. 18, 1984

[54] PREPARATION OF ELECTRICALLY CONDUCTIVE POLYARYLENE COMPOUNDS HAVING ELECTRON-ATTRACTING SIDE GROUPS

[75] Inventors: Herbert Naarmann, Wattenheim; Petr Simak; Gernot Köhler, both of Ludwigshafen, all of Fed. Rep. of Germany

[73] Assignee: BASF Aktiengesellschaft, Fed. Rep. of Germany

[21] Appl. No.: 519,507

[22] Filed: Aug. 2, 1983

[30] Foreign Application Priority Data

Aug. 3, 1982 [DE] Fed. Rep. of Germany ....... 3228880

[51] Int. Cl.³ .............................................. H01B 1/06
[52] U.S. Cl. .................................... 252/500; 252/512;
252/518; 524/408; 524/409; 524/401; 524/438;
528/487; 528/488; 528/490
[58] Field of Search ......................... 252/500, 512, 518;
523/135, 137; 524/408, 409, 401, 438; 528/487,
488, 490

[56] References Cited

U.S. PATENT DOCUMENTS

| | | | |
|---|---|---|---|
| 4,222,903 | 9/1980 | Heeger et al. | 252/518 |
| 4,344,869 | 8/1982 | Blinne et al. | 252/518 |
| 4,375,427 | 3/1983 | Miller et al. | 252/500 |
| 4,395,497 | 7/1983 | Naarman et al. | 252/518 |
| 4,440,669 | 4/1984 | Ivory et al. | 252/518 |

*Primary Examiner*—Josephine L. Barr
*Attorney, Agent, or Firm*—Keil & Weinkauf

[57] ABSTRACT

Electrically conductive polymeric systems having electrical conductivities greater than $10^{-4}$ S/cm are prepared by a method wherein a polyarylene compound which contains one or more chain members of the formula

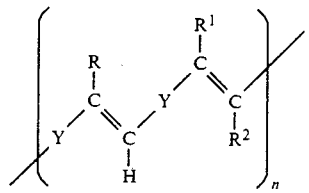

where n is greater than 1, preferably from 5 to 50, R is a nitrile, acid amide, carboxyl or ester group, $R^1$ and $R^2$ are each hydrogen or a nitrile, acid amide, carboxyl or ester group, with the proviso that in each case one of the radicals $R^1$ and $R^2$ is hydrogen and the other is a nitrile, acid amide, carboxyl or ester group, and Y is an aromatic radical, preferably phenylene, is doped, in the absence of moisture and oxygen, with from 0.03 to 0.9 mole percent of an electron-attracting or electron-donating complexing agent. The resulting electrically conductive polymeric systems are useful in the electrical industry for the production of solar cells, for converting and fixing electromagnetic radiation and for the production of electrical and magnetic switches and electrical storage devices, and can be used for the antistatic treatment of plastics.

5 Claims, No Drawings

PREPARATION OF ELECTRICALLY CONDUCTIVE POLYARYLENE COMPOUNDS HAVING ELECTRON-ATTRACTING SIDE GROUPS

The present invention relates to a process for the preparation of electrically conductive polymeric systems having electrical conductivities greater than $10^{-4}$ S/cm by treating a polyarylene compound, in the absence of moisture and oxygen, with from 0.03 to 0.9 mole percent, based on the polyarylene compound employed, of a strong Lewis acid having a $pK_s$ of from $-10$ to $+4$, or of an alkali metal.

Doping with the strong Lewis acid or the alkali metal leads to an increase in the electrical conductivity of the polyarylene compound.

German Laid-Open Application DOS No. 2,947,797 discloses that the electrical conductivity of a polyene compound which contains one or more chain members of the formula

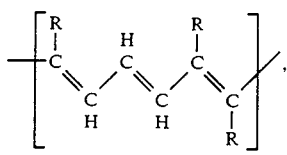

where R is hydrogen or methyl, and seven or more aliphatic double bonds, can be increased by treating this compound, in the absence of moisture and oxygen, with from 0.03 to 0.9 mole percent of a strong Lewis acid, eg. $AsF_5$, $Sbf_5$, $FSO_3H$, $HCLO_4$, $NO^+AsF_6^-$, or of an alkali metal. The resulting conductive polyene compound is extremely sensitive to moisture and atmospheric oxygen.

Furthermore, German Laid-Open Application DOS No. 2,947,796 and Polymer, 20 (1979), 1441-1443 disclose that the electrical conductivity of poly(-phenylenevinylenes) of the formula —Ph-CH=CH— can be increased by doping them with alkali metals or strong Lewis acids, eg. $AsF_5$. However, these electrically conductive systems, too, are unstable in the presence of oxygen and/or water, and rapidly lose their conductivity when exposed to air at room temperature (cf. Polymer, Loc. cit).

German Laid-Open Application DOS No. 3,114,342 proposes preparing electrically conductive polyene systems which are more stable to hydrolysis and to oxygen by a method in which a polyene compound which has a purely aliphatic polymer main chain substituted by nitrile, acid amide or phenyl groups is doped with an alkali metal or a strong Lewis acid.

It is an object of the present invention to provide electrically conductive polyarylene compounds which can be prepared in a simple manner by doping by a prior art method, and are more stable to hydrolysis, possess improved processability and in addition are very stable to atmospheric oxygen and heat.

We have found that this object is achieved, in accordance with the invention, if the polyarylene compound which is doped with an electron-attracting or an electron-donating complexing agent contains one or more chain members of the formula

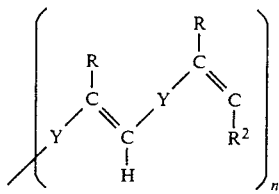

where n is greater than 1, preferably from 5 to 50, R is a nitrile, acid amide, carboxyl or ester group, $R^1$ and $R^2$ are each hydrogen or a nitrile, acid amide, carboxyl or ester group, with the proviso that in each case one of the radicals $R^1$ and $R^2$ is hydrogen and the other is a nitrile, acid amide, carboxyl or ester group, and Y is an aromatic radical, preferably phenylene.

For the purposes of the present invention, electrically conductive polymeric systems having electrical conductivities greater than $10^{-4}$ S/cm are substances which have an electrical conductivity greater than $10^{-4}$ S/cm as measured by the method of F. Beck, Ber. Bunsenges. 68 (1964), 558-567.

The polyarylene compound employed according to the invention is treated, using a conventional method and in the absence of moisture and oxygen, with, as the complexing agent, from 0.03 to 0.9 mole percent, based on the polyarylene compound employed, of, in particular, a strong Lewis acid having a $pK_s$ of from $-10$ to $+4$ or of an alkali metal.

Examples of suitable Lewis acids having a $pK_s$ of from $-10$ to $+4$ (n complexing agents) are $AsF_5$, $SbF_5$, $HCLO_4$, $FSO_3H$, $CLO_2$, $NO^+SbF_6^-$, $NO_2^+SbF_6^-$, $NO^+AsF_6^-$, $NO_2^+AsF_6^-$, $NO^+PF_6^-$, $NO_2^+PF_6^-$, $NO^+BF_4^-$, $NO_2^+BF_4^-$, $NO^+CLO_4^-$, $(CF_3)_2SO_4$, 2,4,6-trinitrophenol, 2,4,6-trinitrobenzenesulfonic acid and 2,4,6-trinitrobenzoic acid.

Examples of alkali metals (p complexing agents) which are used are sodium and potassium; these can also be employed in the form of a solution, for example in naphthalene or α-methylstyrene.

The treatment of the polyarylene compound with the Lewis acid or alkali metal is carried out at from $-70°$ to $150°$ C., preferably from $-10°$ to $100°$ C., in particular from $0°$ to $30°$ C. The Lewis acid or alkali metal which undergoes complex formation with the polyarylene to give the electrically conductive system is used in an amount of from 0.03 to 0.9, preferably from 0.1 to 0.5, mole percent, based on the polyarylene compound.

The complexing agent is incorporated in the absence of moisture (water) and oxygen (air), so that the reaction is preferably carried out under a noble gas atmosphere (argon). If required, non-aqueous solvents which do not react with the complexing agent under the process conditions, e.g. methylene chloride, tetrahydrofuran, dimethoxyglycol, nitromethane, naphthalene or α-methylstyrene, are employed as auxiliary liquids. In the novel process, the electrically conductive polyarylenes, which generally have a deep coloration, are formed in the course of from a few seconds to a few minutes. Any solvents which may have been used are advantageously stripped off under reduced pressure at below $100°$ C.

In the novel process, the polyarylene compounds employed contain one or more chain members of the formula

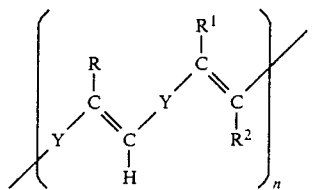

where n is greater than 1, preferably from 5 to 50, R is a nitrile, acid amide, carboxyl or ester group, $R^1$ and $R^2$ are each hydrogen or a nitrile, acid amide, carboxyl or ester group, with the proviso that in each case one of the radicals $R^1$ and $R^2$ is hydrogen and the other is a nitrile, acid amide, carboxyl or ester group, and Y is an aromatic radical, preferably phenylene. The polyarylene compounds used according to the invention are known per se and can be prepared as described in German Laid-Open Application DOS No. 1,618,733. Advantageously, an aromatic dialdehyde, eg. terephthalic dialdehyde, is heated at the boil for not more than 8 hours with, for example, succinodinitrile and/or 1,2-diphenylethane in a molar ratio of 1:1, in the presence of a base, eg. sodium amide or potassium tert.-butylate, in toluene.

Polyarylene compounds which are particularly suitable for the novel process are those of the formulae I to X below.

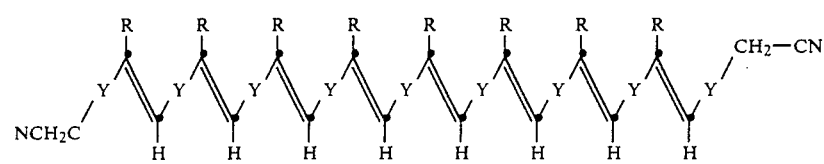 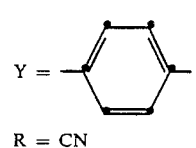 I

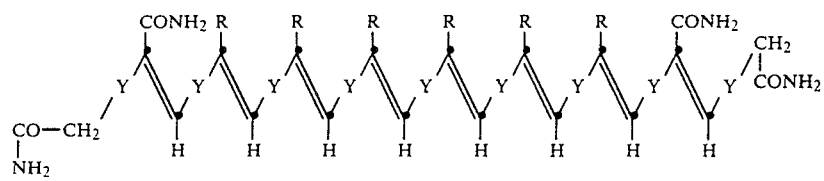 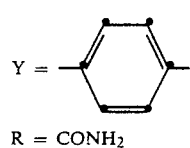 II

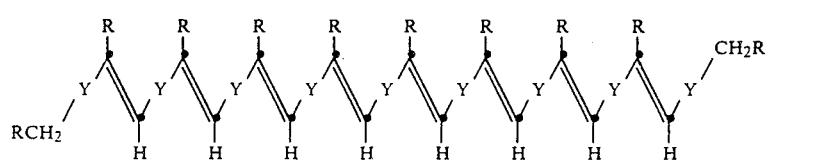 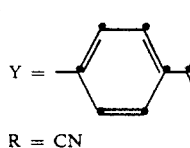 III

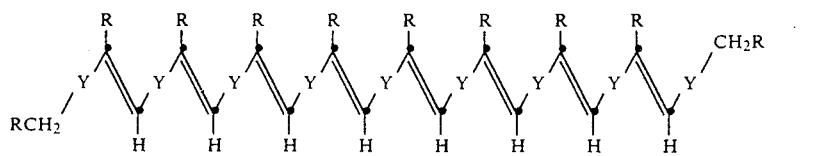 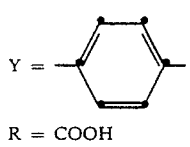 IV

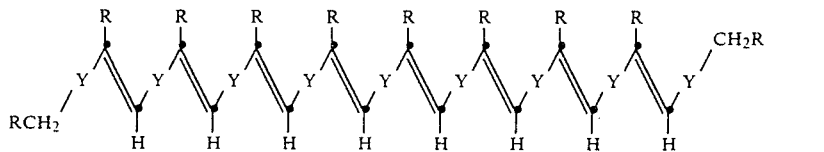 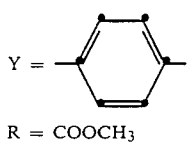 V

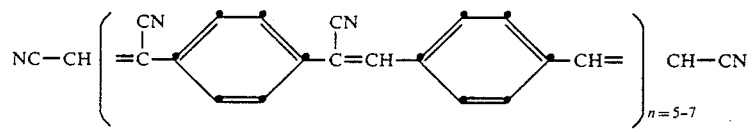 VI

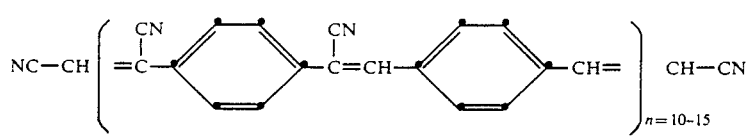 VII

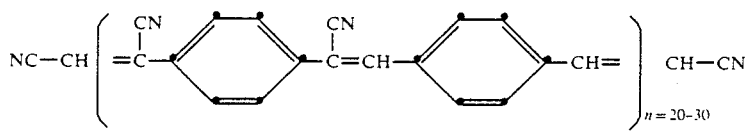 VII

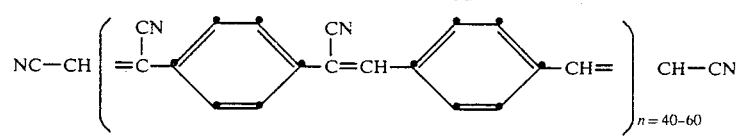

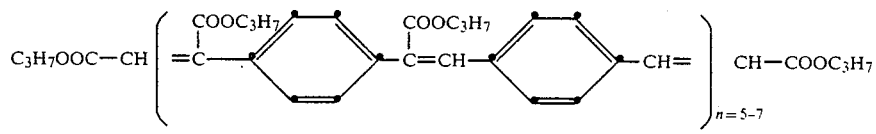

The electrically conductive polyarylenes prepared according to the invention are useful for the antistatic treatment of plastics, for the production of solar cells, for converting and fixing electromagnetic radiation and for the production of electrical and magnetic switches and electrical storage devices.

In the Examples which follow, parts are by weight.

EXAMPLES 1 to 12

An n or p complexing agent was added to 10 parts of the particular polyarylene compound under argon, at room temperature and in the absence of moisture and atmospheric oxygen. Complex formation took place immediately. The resulting deep bluish black crystalline compound had a conductivity of $> 10^{-4}$ S/cm, measured in a conductivity cell. The conductivity of the initial polyarylene was about $10^{-10}$ S/cm. The polyarylenes and complexing agents used in the individual examples, and the electrical conductivities of the resulting products, are shown in the Table, where the numbering of the polyarylenes corresponds to that used in the description above.

| Example | Polyarylene, type and amount | Initial conductivity at 25° C. [S/cm] | Complexing agent, amount [parts] and type | Conductivity after doping, at 25° C. [S/cm] |
|---|---|---|---|---|
| 1 | I<br>10 parts | $1.0 \cdot 10^{-10}$ | 15 SbF$_5$<br>about 0.1 mole % | $4.2 \cdot 10^{-3}$ |
| 2 | II<br>10 parts | $1.4 \cdot 10^{-10}$ | 15 SbF$_5$<br>about 0.1 mole % | $2.5 \cdot 10^{-3}$ |
| 3 | III<br>10 parts | $1.4 \cdot 10^{-10}$ | 18 NO$^+$SbF$_6$<br>about 0.1 mole % | $2.8 \cdot 10^{-3}$ |
| 4 | IV<br>10 parts | $1.4 \cdot 10^{-10}$ | 20 NO$_2$$^+$SbF$_6$<br>about 0.1 mole % | $3.6 \cdot 10^{-3}$ |
| 5 | V<br>10 parts | $1.4 \cdot 10^{-10}$ | 6 K<br>about 0.2 mole % | $2.0 \cdot 10^{-2}$ |
| 6 | VI<br>10 parts | $3.5 \cdot 10^{-10}$ | 20 SbF$_5$<br>about 0.2 mole % | $6.5 \cdot 10^{-2}$ |
| 7 | VII<br>10 parts | $2.4 \cdot 10^{-10}$ | 15 AsF$_5$<br>about 0.1 mole % | $8.5 \cdot 10^{-1}$ |
| 8 | VIII<br>10 parts | $1.0 \cdot 10^{-10}$ | 21 SbF$_5$<br>about 0.2 mole % | $5.0 \cdot 10^{-2}$ |
| 9 | IX<br>10 parts | $1.0 \cdot 10^{-10}$ | 15 AsF$_5$<br>about 0.1 mole % | $0.5 \cdot 10^{-1}$ |
| 10 | I<br>10 parts | $1.0 \cdot 10^{-10}$ | 5 Na<br>about 0.2 mole % | $2.5 \cdot 10^{-3}$ |
| 11 | I<br>10 parts | $1.0 \cdot 10^{-10}$ | 5 AsF$_5$<br>about 0.05 mole % | $3.5 \cdot 10^{-2}$ |
| 12 | I<br>10 parts | $1.0 \cdot 10^{-10}$ | 5 NO$_2$$^+$PF$_6$$^-$<br>about 0.05 mole % | $2.0 \cdot 10^{-1}$ |

We claim:

1. A process for the preparation of an electrically conductive polymeric system having an electrical conductivity greater than $10^{-4}$ S/cm which comprises: treating a polyarylene compound, in the absence of moisture and oxygen, with from 0.03 to 0.9 mole percent, based on the polyarylene compound employed, of a complexing agent of the group of strong Lewis acids having a pK$_s$ of from $-10$ to $+4$ or sodium or potassium, wherein the polyarylene compound employed contains one or more chain members of the formula

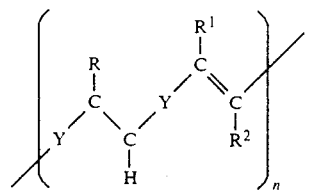

where n is greater than 1 and not greater than 50, R is a carbonnitrile, carboxylicamide, carboxylic or caboxylic ester group, R$^1$ and R$^2$ are each hydrogen or a carbonitrile, carboxylamide, carboxylic or carboxylic ester group, with the proviso that in each case one of the radicals R$^1$ and R$^2$ is hydrogen and the other is a nitrile, acid amide, carboxyl or ester group, and Y is a phenylene or diphenylene radical.

2. The process of claim 1, wherein n is from 5 to 50.

3. The process of claim 1, wherein Y is phenylene.

4. The process of claim 1, wherein the alkali metal, sodium or potassium, is used as the electron-donating complexing agent.

5. The process of claim 1, wherein the complexing agent is used in an amount of from 0.1 to 0.5 mole %, based on the polyarylene compound employed.

* * * * *